United States Patent
Grubbs et al.

(10) Patent No.: US 6,752,964 B1
(45) Date of Patent: Jun. 22, 2004

(54) POLYMER/PLASTICIZER BASED SENSORS

(75) Inventors: Robert H. Grubbs, South Pasadena, CA (US); Nathan S. Lewis, La Canada, CA (US); Adam J. Matzger, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/338,339

(22) Filed: Jun. 22, 1999

Related U.S. Application Data

(60) Provisional application No. 60/090,412, filed on Jun. 23, 1998.

(51) Int. Cl.[7] .............................................. G01N 27/00
(52) U.S. Cl. .................. 422/98; 422/82.01; 422/82.02; 422/82.03; 422/83; 204/412; 204/415; 204/416; 204/418; 204/431; 436/149; 436/151
(58) Field of Search ........................... 422/82.01, 82.02, 422/82.03, 82.05, 82.06, 82.07, 83, 90, 98; 204/412, 415, 416, 418, 431; 436/149–151

(56) References Cited

U.S. PATENT DOCUMENTS

| | | | |
|---|---|---|---|
| 4,587,101 A | | 5/1986 | Marsoner et al. ............. 422/56 |
| 4,599,609 A | | 7/1986 | Blanchard ................... 342/602 |
| 4,925,544 A | | 5/1990 | Goldring .................... 204/421 |
| 5,043,286 A | * | 8/1991 | Khalil et al. ................ 436/136 |
| 5,173,432 A | * | 12/1992 | Lefkowitz et al. .......... 436/138 |
| 5,336,388 A | | 8/1994 | Leader et al. ............... 204/406 |
| 5,374,562 A | * | 12/1994 | Simon ........................ 436/131 |
| 5,405,583 A | * | 4/1995 | Goswami et al. ............. 422/86 |
| 5,480,611 A | * | 1/1996 | Mills et al. .................... 422/55 |
| 5,554,339 A | | 9/1996 | Cozzette et al. .............. 422/50 |
| 5,571,401 A | * | 11/1996 | Lewis et al. ................. 205/787 |
| 5,658,444 A | * | 8/1997 | Black et al. ................. 204/415 |
| 5,738,774 A | * | 4/1998 | Harrison et al. ............ 204/418 |
| 5,871,671 A | | 2/1999 | Kinlen et al. ................ 252/500 |
| 5,911,862 A | | 6/1999 | Chan .......................... 204/418 |
| 6,004,442 A | * | 12/1999 | Choulga et al. ............ 204/416 |
| 6,033,630 A | | 3/2000 | Hinton et al. ................. 422/98 |

FOREIGN PATENT DOCUMENTS

| | | | |
|---|---|---|---|
| WO | WO 96/29594 | 9/1996 | .......... G01N/27/12 |

OTHER PUBLICATIONS

Buhlmann, et al., "Plasticised polymeric electrolytes: new extremely versatile receptor materials for gas sensors (VOC monitoring) and electronic noses (odour identification/discrimination)", *Sensors and Actuators B*, 49:156–165 (1988).

Buhlmann et al.; "Clathrates as coating materials for dielectric transducers with regard to organic solvent vapour sensors"; *Sensors and Actuators*, B 26–27 (1995) pp. 158–161.

Ke–Min Wang, et al., Piezoelectric Crystal Sensor With a Plasticized Poly(Vinyl Chloride) Coating for Determination of Trace Amounts of Ethanol Vapour, Analyst, Feb. 1996, vol. 121, pp. 259–262.

* cited by examiner

*Primary Examiner*—Jill Warden
*Assistant Examiner*—Dwayne K. Handy
(74) *Attorney, Agent, or Firm*—Townsend and Townsend and Crew LLP

(57) ABSTRACT

This invention relates to a novel class of vapor sensors with tunable properties. More particularly, this invention relates to vapor sensors modified by the addition of a compatible small molecule of low volatility, i.e., a plasticizer. In certain aspects, the invention relates to a sensor for detecting an analyte in a fluid comprising: an organic polymer; a plasticizer combined with the organic polymer; and detector operatively associated with the organic polymer.

21 Claims, No Drawings

POLYMER/PLASTICIZER BASED SENSORS

CROSS-REFERENCES TO RELATED APPLICATIONS

The present application claims priority to U.S. Application Serial No. 60/090,412, filed Jun. 23, 1998, the disclosure of which is hereby incorporated by reference in its entirety.

STATEMENT AS TO RIGHTS TO INVENTIONS MADE UNDER FEDERALLY SPONSORED RESEARCH AND DEVELOPMENT

The research embodied in the present application was supported in part by grant No. DAAK60-97-K-9503 awarded by the United States Army. The government may have rights in any patent issuing on this application.

FIELD OF THE INVENTION

This invention relates to a novel class of vapor sensors with tunable properties. More particularly, this invention relates to vapor sensors modified by the addition of a compatible small molecule of low volatility, i.e., a plasticizer.

BACKGROUND OF THE INVENTION

There is considerable interest in developing chemically sensitive sensors that are capable of detecting the presence of a particular chemical analyte in a fluid. Because the fluid is typically air, such sensors act as electronic noses, "smelling" the presence of a particular airborne molecule. These sensors are often fabricated from a polymeric organic material that is capable of absorbing a chemical analyte which comes in contact therewith, wherein absorbance of the analyte causes the polymeric material to expand or change, thereby modifying the electrical properties of the sensor. Variability in the ability to absorb an analyte results in variability in the detectable signal produced. Such organic polymer-based sensors have found use in a variety of different applications and devices including, for example, devices that function as analogs of the mammalian olfactory system (see, U.S. Pat. No. 5,571,401, which issued to Lewis et al, Lundström et al., *Nature* 352:47–50 (1991) and Shurmer and Gardner, *Sens. Actuators* B 8:1–11 (1992)), bulk conducting polymer films (Barker et al., *Sens. Actuators* B 17:143 (1994) and Gardner et al., *Sens. Actuators* B 18:240 (1994)), surface acoustic wave devices (Grate et al., *Anal. Chem.* 67:2162 (1995), Grate et al., *Anal. Chem.* 65:A987 (1993) and Grate et al, *Anal. Chem.* 65:A940 (1993)), fiber optic micromirrors (Hughes et al., *J. Biochem. and Biotechnol.* 41:77 (1 993)), quartz crystal microbalances (Chang et al., *Anal. Chim. Acta* 249:323 (1991)) and dye impregnated polymeric coatings on optical fibers (White et al, *Anal. Chem.* 68:2191 (1996)). To date, however, many of the sensors employed in the above-described devices have been fabricated from limited numbers of polymeric components and, therefore, are limited in the responses they are capable of producing.

Further, today's technology lags far behind the ability of canines or humans to detect or distinguish between chemical analytes. As a consequence, certain work is limited by the suitability of animals or humans to execute tasks. For example, quality control of food products can require production line employees to smell each item. Unfortunately, the ability of individuals to adequately discriminate odors diminishes after a short period of time, e.g., in about two hours. In addition, mammalian olfactory senses are limited in their ability to identify certain vapors. For example, water vapor is not detectable by smell. FurthFurther, mammalian olfactory senses are limited to identifying gaseous components, with no ability to identify or "smell" solutes in liquids.

Recent studies have shown that arrays of chemically sensitive sensors, such as those disclosed in U.S. Pat. No. 5,571,401, formed from a library of expandable insulating organic polymers containing a conductor such as carbon black, are broadly responsive to a variety of analytes, yet allow classification and identification of organic vapors through application of pattern recognition methods. (Lonergan et al., *Chem. Mater.* 8:2298 (1996)). To date, these array elements have been fabricated from a relatively small number of approximately 10–20 organic polymers, with a single distinct polymer backbone composition in each sensor element. Although a limited number of polymeric sensor compositions might be chosen to perform optimally for specific applications, attempts to perform complex applications, such as to mimic the sense of olfaction, in which the sensing task is time dependent or is not defined in advance of the sensor array construction, will almost certainly require use of polymeric sensor libraries that are far more extensive and compositionally diverse than those presently known.

In general, plasticizers are organic compounds added to polymers to facilitate processing and to increase the flexibility and toughness of the polymeric product. Among the more important plasticizers are nonvolatile organic liquids and low melting solids such as phthalates, adipate and sebacate esters, polyols such as ethylene glycol and tricresyl phosphates.

U.S. Pat. No. 4,948,490, which issued to Venkatasetty, discloses a single cell electrochemical sensor utilizing a conducting polymeric solid electrolyte film. These conducting polymeric films such as polyethylene oxide, polypropylene oxide and polyvinylidine fluoride can be used with a plasticizer. A preferred plasticizer is polyethylene glycol dimethyl ether. The plasticizer is added to the mixture to increase ionic conductivity by converting some or substantially all of the structure from crystalline to a plasticized amorphous form.

In addition, U.S. Pat. No. 4,587,101, discloses a fluorescence oxygen sensor having a plasticized polymer with fluorescent indicator molecules embedded within the polymer. In operation, the presence of the oxygen reduces the intensity of the fluorescent indicator substance, thus facilitating detection.

European Patent Application No. 0 794 428, published Sep. 10, 1997, describes sensors capable of distinguishing between enantiomers. The sensor comprise a pair of spaced apart contacts and a conducting polymer material spanning the gap. The polymer has chiral sites in the polymer material formed by incorporating optically active counter ions such as camphor sulfonic acid.

WO 99/00663, published Jan. 7, 1999, the contents of which are incorporated by reference herein, discloses a sensor in which at least a first and second organic polymer are combined to form an organic polymer blend. The sensor will preferably provide a signal that is not linearly related to the mole fraction of at least one of the organic polymers used to produce the organic polymer blend.

In view of the foregoing, and despite the advances disclosed in WO 99/00663, there still remains a need for novel methods for producing large libraries of radically sensitive sensors having tunable properties, each of which are capable of producing a detectable response in the presence of an analyte of interest. The present invention fulfills this and other needs.

SUMMARY OF THE INVENTION

In accordance with the present invention, a novel organic polymer-based sensor is provided with tunable properties capable of detecting the presence of an analyte in a fluid, thereby providing a detectable response. As used herein, the term "fluid" includes gases, vapors, solids, and liquids. As used herein, the term "tunable" refers to tailoring a sensor to a specific application with specific types of polymers and constituents thereof. In certain embodiments, the sensor comprises an organic mixture and a detector operatively associated with the mixture. In one embodiment, the organic mixture comprises a compatible molecule of low volatility (a plasticizer) combined with an insulating organic polymer or a conducting organic polymer. In another embodiment, the organic mixture comprises a plasticizer combined with an organic polymer blend of a first organic polymer and a second organic polymer. In certain embodiments, the first or second polymers are both insulating polymers. In still another embodiment, the organic mixture comprises a plasticizer combined with an organic polymer formed from a first organic monomer and a second monomer. In yet another embodiment, the organic mixture comprises a plasticizer combined with an interpenetrating network comprising a first organic polymer and a second organic polymer formed from an organic monomer polymerized in the presence of the first organic polymer.

In another embodiment of the present invention, an electrically conductive material, which can be a single electrically conductive material or a mixture of two or more electrically conductive materials, is added to the organic mixture, such as an insulating organic polymer. In a preferred embodiment, the electrically conductive material is carbon black. In certain instances, the sensors are arranged in regions of conducting material and insulating material, such as in a matrix. In such embodiments, when the electrically conductive material is added to the organic mixture, the resulting sensor has a first electrical response in the absence of an analyte and a second electrical response in the presence of an analyte. In certain instances, the detector is an electrical measuring device electrically coupled to the sensor to measure the first and second electrical responses. Other suitable responses that can be detected include, but are not limited to, electrical responses, such as resistance, impedance, capacitance, optical response, magnetic response, surface acoustic response and fluorescence response.

In yet another embodiment of the present invention, sensor arrays are constructed with at least a first and a second sensor wherein each sensor comprises a polymer, such as an organic polymer (e.g., insulating or conducting). At least one of the first and second sensors includes a plasticizer combined with the polymer. A detector is operatively associated with each sensor. In a preferred embodiment, an organic material is mixed with an electrically conductive material. In such embodiments, the detector is an electrical measuring device electrically coupled to the sensor to measure the first and second electrical resistances.

In still yet another embodiment of the present invention, sensor arrays are constructed with at least a first and a second sensor wherein each sensor comprises a polymer, such as an organic polymer, such as an insulating organic polymer. At least one of the first and second sensors includes a plasticizer combined with the polymer. A detector is operatively associated with each sensor. In such embodiments, the detector is an electrical measuring device electrically coupled to the sensor to measure the first and second electrical responses.

Methods of using the sensors are also provided. One embodiment is a method for detecting the presence of an analyte in a fluid, the method includes, providing a sensor array comprising a plurality of sensors wherein each sensor in the plurality comprises a polymer, such as an organic polymer, and wherein at least one sensor in the plurality further comprises a plasticizer mixed with the polymer. A detector is operatively associated with each sensor. The detector can detect variations in, for example, electromagnetic energy, optical properties, resistance, capacitance, inductance or impedance of a combination thereof, and other physical, chemical and electrical properties that can vary in accordance with the response of the sensors. The sensors are then exposed to a fluid containing an analyte and the sensor responses measured. The sensor responses are compared to determine the presence of an analyte in the fluid. In a preferred embodiment, the polymer in the sensors includes an electrically conducting material, preferably carbon black, wherein the sensor response to the presence of the analyte, is a change in a resistance associated with the sensor. In such embodiments, the detector is an electrical measuring apparatus electrically coupled to the sensors, measuring an electrical response of each sensor. These and other embodiments will become more apparent when read with the accompanying detailed description of the invention.

DETAILED DESCRIPTION OF THE INVENTION AND PREFERRED EMBODIMENTS

In certain aspects, the present invention provides methods for producing large libraries of sensors having tunable properties, each of which are capable of producing a detectable response in the presence of an analyte of interest. In the presence of an analyte, a sensor comprising a polymer such as an organic polymer, will sorb the analyte, producing a detectable response in the polymer. A detector operatively associated with the sensor detects the response. In certain embodiments, the polymer is nonconductive and is mixed with an electrically conductive material. In certain instances, the sensor comprises nonconductive regions of organic polymer, such as insulating organic polymer, interspersed with regions of electrically conductive material. As the nonconductive region (or insulating phase) of the sensor sorb an analyte, the properties, such as resistance, of the sensor changes.

Arrays of such sensors are disclosed in U.S. Pat. No. 5,571,401, which issued to Lewis, et al. Many different polymers can be used. Suitable insulating organic polymers include, but are not limited to, main-chain carbon polymers such as poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitriles), poly(vinyl esters), poly(styrenes), poly(arylenes), and the like, main-chain acrylic heteroatom organic polymers such as poly(oxides), poly(carbonates), polyesters), poly(anhydrides), poly(urethanes), poly(sulfonates), poly(siloxanes), poly(sulfides), poly(thioesters), poly(sulfones), poly(sulfonamides), poly(amides), poly(ureas), poly(phosphazenes), poly(silanes), poly(silazanes), and the like, and main-chain heterocyclic polymers such as poly(furan tetracarboxylic acid diimides), poly(benzoxazoles), poly (oxadiazoles), poly(benzothiazinaphenothiazines), poly (benzothiazoics), poly(pyrazinoquinoxalines), poly (pyromellitimides), poly(quinoxalines), poly (benzimidazoles), poly(oxindoles), poly(oxoisoindolines), poly(dioxoisoindolines), poly(triazines), poly(pyridazines), poly(piperazines), poly(pyridines), poly(piperidines), poly (triazoles), poly(pyrazoles), poly(pyrrolidines), poly (carboranes), poly(oxabicyclononanes), poly (dibenzofarans), poly(phthalides), poly(acetals), poly (anhydrides), carbohydrates, and the like. In a preferred embodiment, the polymers employed are poly(vinyl acetate) (PVA) and poly(methacrylate) (PMMA) and polystyrene (PS). Each of the above organic polymers, and the monomer units that polymerize to form these polymers, are well known to those of skill in the art.

One or more of a variety of electrically conductive materials can be employed as the electrically conductive material. In some embodiments, the conductive material is an organic conducting polymer. Examples of such organic conducting polymers include, but are not limited to, poly (anilines), poly(thiophenes), poly(pyrroles), poly (acetylenes), and the like. In other embodiments, the conductive material is a carbonaceous material such as carbon blacks, graphite, coke, $C_{60}$, and the like. In a preferred embodiment, the conductive material is carbon black. In an equally preferred embodiment, the conductive material can be a particle, such as a gold nanoparticle with a capping ligand shell (see, WO 99/27357 incorporated herein by reference). In still other embodiments, the conductive material is a charge transfer complex such as tetramethylparaphenylenediamine-chloranile, alkali metal tetracyanoquinodimethane complexes, tetrathiofilvalene halide complexes, and the like. In other embodiments, the conductive material is an inorganic conductor such as a metal or a metal alloy. Examples include, but are not limited to, Ag, Au, Cu, Pt, AuCu alloy, and the like. In other embodiments, the conductive material is a highly doped semiconductor. Examples include, but are not limited to, Si, GaAs, InP, $MoS_2$, $TiO_2$, and the like. In still other embodiments, the conductive material is a conductive metal oxide. Examples include, but are not limited to, $In_2$, $O_3$, $SnO_2$, Na, Pt, $O_4$, and the like. In other embodiments, the conductive material is a superconductor, examples include, but are not limited to, $YBa_2Cu_3,O_7$, $Tl_2Ba_2$, $Ca_2Cu_3O_{10}$, and the like. In still other embodiments, the conductive material is a mixed inorganic/organic conductor. Examples include, but are not limited to, tetracyanoplatinate complexes, iridium halocarbonyl complexes, stacked macrocyclic complexes, and the like.

Applicants have surprisingly discovered that by combining the organic polymer with a plasticizer, the response of the sensor to a particular analyte is changed. Note that U.S. Pat. No. 5,571,401 discloses the addition of a "plasticizer" to the organic polymer within its disclosed sensor array. See, e.g., Column 11, Table 3. These compounds, high molecular weight polymers such as polystyrene, were "plasticizers" in the sense that they were added to the organic polymer and affected its resulting structure. However, such compounds are not normally considered plasticizers. For example, *Hawley's Condensed Chemical Dictionary,* 11th Ed., defines "plasticizer" as: "An organic compound added to a high molecular weight polymer both to facilitate processing and to increase the flexibility and toughness of the final product by internal modification (salvation) of the polymer molecule." High molecular weight polymers such as those disclosed in Table 3 of U.S. Pat. No. 5,557,401 would not fall within this definition, which definition is adopted herein for all following references to "plasticizer."

Suitable plasticizers for use in the present invention include, but are not limited to, phthalates and their esters, adipate and sebacate esters, polyols such as polyethylene glycol and their derivatives, tricresyl phosphate, castor oil, camphor etc. Those of skill in the art will be aware of other plasticizers suitable for use in the present invention.

The discovery that plasticizers affect the resulting responses in sensors containing polymers such as organic polymers leads to important advantages. For example, machine olfaction or electronic "noses" will require the use of a large number of chemically distinct organic polymeric compounds. By the addition of a plasticizer, the number of such chemically distinct organic polymeric compounds is greatly increased. For example, consider a sensor array comprising five distinct organic compounds (and thus five different sensors). With the addition of five distinct plasticizers, the number of compositionally distinct sensors is increased from five to thirty. Moreover, the number of compositionally distinct sensors can be further increased if the plasticizer is added to an organic polymer formed as a blend of a first organic polymer and a second organic polymer. Alternatively, the plasticizer can be added to an organic polymer formed from a first organic monomer and a second organic monomer.

In certain embodiments, the plasticizers of the present invention are chiral plasticizers i.e., the plasticizer contains at least one asymmetric center. In certain aspects, the polymers containing a chiral plasticizer can be a conductive polymer, a nonconductive polymer or both a conductive polymer and a nonconductive polymer. Chiral plasticizers enable the discrimination and detection of optical isomers or analytes containing an asymmetric center by the sensors of the present invention.

The plasticizer can also be added to an organic polymer forming an interpenetrating network (IPN) comprising a first organic polymer and a second organic polymer formed from an organic monomer polymerized in the presence of the first organic polymer. This technique works particularly well when dealing with polymers that are imiscible in one another, where the polymers are made from monomers that are volatile. Under these conditions, the preformed polymer is used to dictate the properties (e.g., viscosity) of the polymer-monomer mixture. Thus, the polymer holds the monomer in solution. Examples of such a system are (I) polyvinyl acetate with monomer methylmethacrylate to form an IPN of pVA and pMMA, (2) pVA with monomer styrene to form an IPN of pVA and polystyrene, and (3) pVA with acrylonitrile to form an IPN of pVA and polyacrylonitrile. Each of the example compositions would be modified by the addition of an appropriate plasticizer. More than one monomer can be used where it is desired to create an IPN having one or more copolymers.

In certain instances, the sensors comprising plasticizers show an increased response rate, such as an electrical response rate in the presence of an analyte, compared to sensors without plasticizers. An increased sensor response rate is advantageous especially when performing multiple sampling because the recycle time is increased dramatically. By speeding the recovery rate of individual sensors, the sampling time is increased dramatically.

The present invention provides methods for the rapid construction of large libraries of sensors through combinatorial techniques. Combinatorial chemistry is a generic term that describes a series of innovative technologies that are designed to automate and simplify the selection, synthesis and fabrication of candidate polymers and plasticizers and combinations thereof into a library. The initial step of a combinatorial process is selection of compounds such as polymers and plasticizers, for inclusion in a library of compounds. A major focus in the synthesis of the library is the automation of each step of various operations. In many cases, 96-well or 384-well microtiter plates are used to dispense reagents. Automated systems are available that control temperature of the reactions, volume of reaction reagents, inertness of the reaction atmosphere, etc. In addition, highly automated sampling handling and analysis has been developed to analyze the volume of compounds in the library.

Preparation of combinatorial chemical libraries is well known to those of skill in the art. Such combinatorial chemical libraries include for instance, peptide libraries (see, e.g., U.S. Pat. No. 5,010,175, Furka, *Int. J. Pept. Prot. Res.* 37:487 (1991), Houghton et al., *Nature,* 354:84 (1991)). Peptide synthesis is by no means the only approach envisioned and intended for use with the methods of the present invention. Other chemistries for generating chemical diversity libraries can also be used. Such chemistries include, but are not limited to: peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs, et al., *Proc. Nat. Acad. Sci. USA* 90:6909 (1993)), vinylogous polypeptides (Hagihara, et al., *J. Amer. Chem. Soc.* 114:6568 (1992)), nonpeptidal peptidomimetics with a α-D-glucose scaffolding (Hirschmann, et al., *J. Amer. Chem. Soc.* 114:9217 (1992)), analogous organic syntheses of small compound libraries (Chen, et al., *J. Amer. Chem. Soc.* 116:2661 (1994)), oligocarbamates (Cho, et al., *Science* 261:1303 (1993)), and/or peptidyl phosphonates (Campbell, et al., *J. Org. Chem.* 59:658 (1994)). See, generally, Gordon, et al., *J. Med Chem.* 37:1385 (1994), nucleic acid libraries, peptide nucleic acid libraries (see, e.g., U.S. Pat. No. 5,539, 083) antibody libraries (see, e.g., Vaughn, et al., *Nature Biotech.* 14(3):309–314 (1996), and PCT/US96/10287), carbohydrate libraries (see, e.g., Liang, et al., *Science* 274:1520 (1996), and U.S. Pat. No. 5,593,853), and small organic molecule libraries (see, e.g., benzodiazepines, Baum, *C&EN,* Jan. 18, 1993 p. 33; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines U.S. Pat. No. 5,288,514, cyclopentane carboxylic acid (cispentacin) compounds (Jethwaney, D., et al., *Microbiology* 143:397 (1997) and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a person of skill in the art. The nature and implementation of modifications to these devices (if any) so that they can operate as discussed herein will be apparent to skilled artisans. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In other embodiments, peptide mimetics, called "peptoids", are assembled and screened for the desired biological activity by a range of methodologies (see, Gordon et al., *J. Med Chem.,* 37:1385–1401 (1994). For example, the method of Geysen, (*Bioorg. Med. Chem. Letters,* 3:397–404 (1993); *Proc. NatL Acad Sci. USA,* 81:3998 (1984)) employs a modification of Merrifield peptide synthesis, wherein the C-terminal amino acid residues of the peptides to be synthesized are linked to solid-support particles shaped as polyethylene pins; these pins are treated individually or collectively in sequence to introduce additional amino-acid residues forming the desired peptides.

Houghton, *Proc. Natl. Acad Sci. USA,* 82:5131 (1985); Eichler et al, *Biochemistry,* 32:11035–11041 (1993); and U.S. Pat. No. 4,631,211) utilizes individual polyethylene bags ("tea bags") containing C-terminal amino acids bound to a solid support. These are mixed and coupled with the requisite amino acids using solid phase synthesis techniques. The peptides produced are then recovered and used individually. Fodor et al., *Science,* 251:767 (1991) described light-directed, spatially addressable parallel-peptide synthesis on a silicon wafer to generate large arrays of addressable peptides that can be directly used. The particulate material of the invention can be utilized in a similar manner.

Parallel synthesis of "small" molecules (non-oligomers with a molecular weight of 200–1000) can also be used. Recently, Ellmann disclosed the solid phase-supported parallel (also referred to as "combinatorial") synthesis of eleven benzodiazepine analogs along with some prostaglandins and beta-turn mimetics. These disclosures are exemplified in U.S. Pat. No. 5,288,514. Another relevant disclosure of parallel synthesis of small molecules can be found in U.S. Pat. No. 5,324,483. This patent discloses the parallel synthesis of between 4 and 40 compounds in each of sixteen different scaffolds. Chen et al. have also applied organic synthetic strategies to develop non-peptide libraries synthesized using multi-step processes on a polymer support. (Chen et al., *J. Am. Chem. Soc.,* 116:2661–2662 (1994)).

Plasticizer polymer sensors provide superior properties as compared to an unmodified organic polymer because of the lowered glass transition temperature in the plasticized organic polymer. Also, the plasticized polymer have superior processing properties, enhanced film stability, increased response rates, lower usable temperature range and greater chemical stability than the unmodified organic polymer. Finally, the plasticizer allow sensor fabrication without the use of volatile solvents because of the superior melt processing properties of the plasticized polymers.

A broad range of analytes can be detected using the sensors of the present invention. Suitable analytes include, but are not limited to, alkanes, alkenes, alkynes, dienes, alicyclic hydrocarbons, arenes, alcohols, ethers, ketones, aldehydes, carbonyls, carbanions, heterocycles, polynuclear aromatics, organic derivatives, biomolecules, microorganisms, bacteria, viruses, sugars, nucleic acids, isoprenes, isoprenoids, fatty acids and their derivatives. In certain embodiments, many biomolecules, such as amino acids, are amenable to detection using the sensor arrays of the present invention.

The sensors of the present invention can be used for a variety of applications. Suitable applications include, but are not limited to, environmental toxicology and remediation, biomedicine, such as microorganism classification or detection, medical diagnosis, material quality control, food and agricultural products monitoring, heavy industrial manufacturing, ambient air monitoring, worker protection, emissions control, and product quality testing.

Various sensors suitable for use in the present invention include, but are not limited to, conducting/nonconducting sensors, bulk conducting polymer films, surface acoustic wave devices, fiber optic micromirrors, quartz crystal microbalances, dye impregnated polymeric coatings on optical fibers, sintered metal oxide sensors, phthalocyanine sensors, Pd-gate MOSFET devices, electrochemical cells, conducting polymer sensors, lipid coating sensors, metal FET structures, carbon black-polymer composites, micro-electro-mechanical system devices, micromachined cantilevers, and a micro-opto-electro-mechanical system devices.

Moreover, various analyses suitable for identifying analytes and quantifying concentration include, but are not limited to, principal component analysis, Fischer linear analysis, neural networks, genetic algorithms, fuzzy logic, pattern recognition, and other algorithms. After analysis is completed, the resulting information is displayed or transmitted to a host computer.

In one illustrative embodiment of the invention, a sensor array was formed as follows. The organic polymer comprised a polymer selected from the group consisting of poly(methyl methacrylate) (PMMA), polystyrene (PS), and poly(vinylchloride) (PVC). The organic polymer was combined with an electrically conductive material, which in this embodiment was carbon black. A plasticizer chosen from the group consisting of di(2-ethylhexyl)phthalate (DOP), diethylene glycol dibenzoate (DGD), glycerol triacetate (GT), tributyl phosphate (TBP), chloroparafin (50% Cl, CP), and tricresyl phosphate (TCP) was added to the organic polymer.

Glass substrates for sensor production were prepared by evaporating 300 Å of chromium followed by 500 Å of gold onto microscope slides masked with a 3 mm strip of drafting tape down the center of the long axis. These were then cut down their short axis to give 15 smaller pieces. Individual sensor elements for PMMA and PVC sensors were prepared by spin coating from a solution of the organic polymer, an appropriate solvent, the plasticizer, and suspended carbon black onto the glass substrates. The electrodes and backs of the slides were cleaned with solvent prior to using the sensors. Five replicates of each sensor were made for each experiment. PS sensors were prepared on surface mount universal boards (surfboards, part 6012 from Capital Advanced Technologies) by dip coating into a solution of the organic polymer, an appropriate solvent, the plasticizer, and suspended carbon black. Those of ordinary skill in the art will appreciate that possible sensor fabrication techniques include spin coating, dip coating, spray coating, and evaporation of a droplet. The following table, Table 1, sets forth the composition of the solutions that were used to either spin or dip coat the sensor substrates. The carbon black used in these solutions was Black Pearls 2000, a furnace material produced by Cabot Co. (Billerica, Mass.). Poly(methyl methacrylate) (PMMA, mw 120,000) and polystyrene (PS, mw 45,000) were purchased from Aldrich Chemical Co. (Milwaukee, Wis.). Poly(vinylchloride) (PVC, raw 275,000) and all plasticizers were obtained from Polysciences, Inc. (Warrington, Pa.).

TABLE 1

| Solution | Polymer/ Solvent | Polymer (mg) | Carbon black (mg) | Plasticizer | Plasticizer (mg) |
|---|---|---|---|---|---|
| A | PMMA/THF | 161 | 39.6 | none | — |
| B | PMMA/THF | 161 | 40.7 | DOP | 39.2 |
| C | PMMA/THF | 161 | 40.3 | DGD | 46.6 |
| D | PMMA/THF | 161 | 40.9 | GT | 38.2 |
| E | PMMA/THF | 161 | 40.5 | TBP | 38.9 |
| F | PMMA/THF | 161 | 40.5 | TBP | 9.4 |
| G | PMMA/THF | 161 | 41.2 | TBP | 18.1 |
| H | PMMA/THF | 161 | 41.1 | TBP | 75.6 |
| I | PS/benzene | 162 | 42.7 | none | — |
| J | PS/benzene | 162 | 40.9 | DGD | 39.0 |
| K | PS/benzene | 162 | 44.5 | CP | 39.3 |
| L | PS/benzene | 162 | 42.6 | TBP | 42.6 |
| M | PS/benzene | 162 | 43.9 | DOP | 43.7 |
| N | PS/benzene | 162 | 41.0 | DOP | 10.0 |
| O | PS/benzene | 162 | 40.0 | DOP | 21.0 |
| P | PS/benzene | 162 | 42.5 | DOP | 80.7 |
| Q | PVC/THF | 160 | 41.0 | none | — |
| R | PVC/THF | 160 | 39.8 | DOP | 40.8 |
| S | PVC/THF | 160 | 40.5 | DGD | 39.71 |
| T | PVC/THF | 160 | 40.4 | TCP | 39.6 |

Note that a letter identified each individual solution.

The sensors prepared from the above solutions were exposed to an analyte, which in this case was the vapor of a number of common solvents. The solvents used as the chemical analyte were hexane, toluene, chloroform, tetrahydrofuran (THF), acetone, ethyl acetate, ethanol, and methanol. In each case, the vapor was diluted to 5% of its vapor pressure. PMMA- and PVC-based sensors were exposed 15 times to each analyte. PS-based sensors were exposed 5 times to each analyte. The analytes were presented in random order. An apparatus for delivering known concentrations of organic vapors was constructed from solvent bubblers, solenoids, and mass flow controllers to precisely control the concentration of the analyte delivered to each sensor. Flow switching and data acquisitions were computer controlled with LabVIEW software.

Sensor resistance measurements as a function of time were recorded before, during, and after analyte exposure using a Keithly model 2002 multimeter attached to a Keithly model 7001 channel switcher. The data were analyzed for the magnitude of the response by subtracting the median of the of the baseline resistance (before analyte exposure) from the median of the resistance (taken at the end of the analyte exposure) and dividing by the baseline resistance. This $\Delta R/R$ was the unique quantity measured for a given sensor during each exposure.

Sensor responses to various solvents were analyzed through the use of a Fisher linear discriminant method. This method provides a measure of the resolving power of a given sensor array for the set of solvents. The result is a matrix of resolution factors describing the ability of the array to distinguish between pairs of solvents.

The effect of added plasticizer is illustrated below in detail for PVC. The results are summarized in tables for each solution that contained PVC, namely solutions Q through T.

|  | Toluene | Chloroform | THF | Acetone | Ethyl Acetate | Ethanol | Methanol |
| --- | --- | --- | --- | --- | --- | --- | --- |
| Solution Q | | | | | | | |
| Hexane | 0.984251 | 0.643293 | 0.842919 | 1.28274 | 0.84445 | 1.53139 | 4.61927 |
| Toluene |  | 0.658509 | 0.807142 | 2.06814 | 1.07682 | 2.4402 | 5.06123 |
| Chloroform |  |  | 0.665612 | 1.4629 | 0.587399 | 1.91321 | 4.9815 |
| THF |  |  |  | 1.45015 | 0.774263 | 1.885012 | 4.91201 |
| Acetone |  |  |  |  | 0.847823 | 0.282196 | 3.98495 |
| Ethyl Acetate |  |  |  |  |  | 1.19 | 4.484 |
| Ethanol |  |  |  |  |  |  | 4.19594 |
| Solution R | | | | | | | |
| Hexane | 4.07487 | 6.50677 | 6.26755 | 12.0878 | 8.62828 | 5.01794 | 7.96911 |
| Toluene |  | 3.37885 | 3.63363 | 6.93624 | 4.22286 | 2.44464 | 6.99162 |
| Chloroform |  |  | 1.0114 | 3.80078 | 0.552501 | 5.14984 | 8.84274 |
| THF |  |  |  | 3.31752 | 1.03253 | 4.57039 | 7.50424 |
| Acetone |  |  |  |  | 4.30155 | 8.64767 | 12.0074 |
| Ethyl Acetate |  |  |  |  |  | 6.12712 | 10.0452 |
| Ethanol |  |  |  |  |  |  | 6.78787 |
| Solution S | | | | | | | |
| Hexane | 0.407902 | 1.45887 | 1.6386 | 4.64552 | 1.66585 | 3.14121 | 4.81276 |
| Toluene |  | 1.31997 | 1.24821 | 4.48867 | 1.44003 | 2.87767 | 5.04127 |
| Chloroform |  |  | 0.532754 | 2.76737 | 0.670284 | 1.54771 | 4.52271 |
| THF |  |  |  | 3.98235 | 0.577512 | 2.30406 | 4.55185 |
| Acetone |  |  |  |  | 3.67577 | 1.52751 | 2.65537 |
| Ethyl Acetate |  |  |  |  |  | 2.10352 | 4.24966 |
| Ethanol |  |  |  |  |  |  | 3.6201 |
| Solution T | | | | | | | |
| Hexane | 3.37051 | 4.88942 | 6.08152 | 9.06222 | 8.40895 | 7.68271 | 9.7596 |
| Toluene |  | 3.44704 | 3.55683 | 7.66181 | 4.70103 | 4.56691 | 6.78456 |
| Chloroform |  |  | 0.721996 | 5.07964 | 0.406391 | 2.66707 | 5.84979 |
| THF |  |  |  | 6.35071 | 0.84786 | 2.71799 | 5.1942 |
| Acetone |  |  |  |  | 6.38207 | 7.5861 | 7.48886 |
| Ethyl Acetate |  |  |  |  |  | 3.52548 | 5.50609 |
| Ethanol |  |  |  |  |  |  | 4.94153 |

The average resolution factor for unplasticized PVC (solution Q) is 2.02. The corresponding numbers for solutions R, S, and T are 2.62, 5.19, and 5.78, respectively. By combining all of the sensors, to make an array with five sensors each from solutions Q-T provides an average resolution factor of 13.11, as demonstrated in the following table.

| | Solutions Q–T | | | | | | |
| --- | --- | --- | --- | --- | --- | --- | --- |
|  | Toluene | Chloroform | THF | Acetone | Ethyl Acetate | Ethanol | Methanol |
| Hexane | 7.42856 | 12.7416 | 13.2806 | 22.0313 | 14.7446 | 10.1892 | 24.025 |
| Toluene |  | 6.10203 | 9.71362 | 12.5442 | 9.43622 | 10.4272 | 15.6674 |
| Chloroform |  |  | 4.49606 | 8.27175 | 6.07853 | 9.70826 | 19.1793 |
| THF |  |  |  | 10.7487 | 4.27985 | 11.0709 | 18.3842 |
| Acetone |  |  |  |  | 10.9168 | 16.8513 | 23.9641 |
| Ethyl Acetate |  |  |  |  |  | 12.3627 | 22.4903 |
| Ethanol |  |  |  |  |  |  | 19.9709 |

The benefits of the present invention are also seen for the PA-based sensor (formed from solutions A–H) and are summarized in the following Table 2.

TABLE 2

| Solution resolution factor | Maximum resolution factor | Minimum resolution factor | Average resolution factor |
|---|---|---|---|
| A | 14.94 | 1.11 | 5.55 |
| B | 18.69 | 1.6 | 9.23 |
| C | 21.26 | 2.74 | 11.37 |
| D | 12.59 | 0.89 | 5.35 |
| E | 16.4 | 0.82 | 6.88 |
| F | 17.7 | 1.67 | 7.78 |
| G | 17.02 | 2.61 | 9.24 |
| H | 19.33 | 1.85 | 7.04 |
| A–D | 78.41 | 9.75 | 32.88 |
| E–H | 59.22 | 7.48 | 7.48 |

Five presentations of each solvent were made for the polystyrene sensors, and qualitative comparison shows that the magnitude of the responses can be affected by the presence of various plasticizers. Sensors made from the plasticized polymer were more likely to be responsive to solvent.

Those of ordinary skill in the art will appreciate that many other embodiments of the invention could be implemented. For example, the concentration of a given plasticizer in a given organic polymer can be varied across a sensor array. Assuming that the sensor response is non-linearly related to the varying plasticizer concentration, additional chemical analyte resolving power will be provided without requiring the use of additional organic polymers or plasticizers. Similarly, the plasticized polymer could be formed from the addition of a plasticizer to an organic polymer blend of a first organic polymer and a second organic polymer. The relative concentration of the first and second organic polymer could be varied in the organic polymer blend, and, assuming a nonlinear sensor response, the resulting sensor array would have greater resolving power.

Many other embodiments exist for sensors that need not include the electrically conductive material with organic polymer and plasticizer mixture. Such sensors can be associated with detectors that measure a response other than the electrical resistance change upon exposure to the chemical analyte. For example, the detector can measure variations in optical transmission through the sensor wherein the detector would be a spectrophotometer. Alternatively, the detectable response is a variation in electromagnetic energy, and the detector measure electromagnetic energy.

All publications, patents and patent applications mentioned in this specification are herein incorporated by reference into the specification in their entirety for all purposes. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A sensor array for detecting an analyte in a vapor or gas, wherein at least one sensor of said array comprises:
   an insulating organic polymer;
   a plasticizer combined with said insulating organic polymer;
   an electrical detector electrically coupled to said organic polymer;
   and a computer with a resident algorithm.

2. A sensor in accordance with claim 1, wherein said insulating organic polymer is formed from a blend of a first organic polymer and a second organic polymer.

3. A sensor in accordance with claim 1, wherein said insulating organic polymer is formed from a first organic monomer and a second organic monomer.

4. A sensor in accordance with claim 1, wherein said insulating organic polymer is formed from an interpenetrating network comprising a first organic polymer and a second organic polymer formed from an organic monomer polymerized in the presence of the first organic polymer.

5. A sensor in accordance with claim 1, further comprising an electrically conductive material added to said organic polymer to form regions conducting and insulating materials and wherein said detector is an electrical measuring device electrically coupled to said insulating organic polymer.

6. A sensor in accordance with claim 5, wherein said electrically conductive material is carbon black.

7. A sensor in accordance with claim 6, wherein said plasticizer is a member selected from the group consisting of di(2-ethylhexyl)phthalate (DOP), diethylene glycol dibenzoate (DGD), glycerol triacetate (GT), tributyl phosphate (TBP), chloroparafin (50% Cl, CP), and tricresyl phosphate (TCP).

8. A sensor in accordance with claim 7, wherein said organic polymer is a member selected from the group consisting of poly(methyl methacrylate) (PMMA), polystyrene (PS), and poly(vinylchloride) (PVC).

9. A system for detecting an analyte in a vapor or gas, said system comprising:
   a sensor array comprising a plurality of sensors wherein at least one of said sensors comprises a plasticizer added to an insulating organic polymer;
   an electrical detector electrically coupled to said sensor array;
   and a computer with a resident algorithm.

10. A system in accordance with claim 9, wherein each of said sensors further comprises an electrically conductive material and wherein said detector is an electrical measuring device electrically coupled to said sensor array.

11. A system in accordance with claim 9, wherein said detector is optimized to detect a member selected from the group consisting of resistance, capacitance, inductance, impedance and combinations thereof.

12. A system in accordance with claim 12, wherein said algorithm of said computer is a member selected from the group consisting of principal component analysis, Fischer linear analysis, neural networks, genetic algorithms, fuzzy logic, pattern recognition, and combinations thereof.

13. A system in accordance with claim 9, wherein at least one of said sensors in said array is a member selected from the group consisting of conducting/nonconducting sensors, bulk conducting polymer films, surface acoustic wave devices, fiber optic micromirrors, quartz crystal microbalances, dye impregnated polymeric coatings on optical fibers, sintered metal oxide sensors, phthalocyanine sensors, Pd-gate MOSFET devices, electrochemical cells, conducting polymer sensors, lipid coating sensors, metal FET structures, carbon black-polymer composites, micro-electro-mechanical system devices, micromachined cantilevers, and micro-opto-electro-mechanical system devices.

14. A method for detecting the presence of an analyte in a vapor or gas, said method comprising:
   providing a sensor array comprising at least one sensor in said array having a polymer with a plasticizer mixed therein;
   contacting said sensor array with said analyte to generate an electrical response;
   detecting said electrical response with a detector that is operatively associated with each sensor, and correlating said electrical response to a known response, thereby detecting the presence of said analyte.

15. A method in accordance with claim 14, wherein said detector is optimized to detect a member selected from the group consisting of resistance, capacitance, inductance, impedance and combinations thereof.

16. A method in accordance with claim 14, wherein said analyte is detected in an application which is a member selected from the group consisting of environmental toxicology, remediation, biomedicine, material quality control, food and agricultural products monitoring, heavy industrial manufacturing, ambient air monitoring, worker protection, emissions control, and product quality testing.

17. A method in accordance with claim 14, wherein said plasticizer is a member selected from the group consisting of phthalates, phthalate esters, adipate esters, sebacate esters, polyols, tricresyl phosphate, castor oil, camphor, di(2-ethylhexyl)phthalate, diethylene glycol dibenzoate, glycerol triacetate, tributyl phosphate, chloroparafin and tricresyl phosphate.

18. A method in accordance with claim 14, wherein said at least one sensors in said sensor array is a member selected from the group consisting of conducting/nonconducting sensors, bulk conducting polymer films, surface acoustic wave devices, fiber optic micromirrors, quartz crystal microbalances, dye impregnated polymeric coatings on optical fibers, sintered metal oxide sensors, phthalocyanine sensors, Pd-gate MOSFET devices, electrochemical cells, conducting polymer sensors, lipid coating sensors, metal FET structures, carbon black-polymer composites, micro-electro-mechanical system devices, micromachined cantilevers, and micro-opto-electro-mechanical system devices.

19. A sensor in accordance with claim 1, wherein said plasticizer is chiral.

20. A sensor array for detecting an analyte in a vapor or gas, wherein at least one sensor of said array comprises:
   an organic polymer;
   a plasticizer combined with said organic polymer; and
   an electrical detector electrically coupled to said organic polymer.

21. A sensor in accordance with claim 20, wherein said plasticizer is a chiral plasticizer.

* * * * *